United States Patent
Livnat

(10) Patent No.: US 10,433,720 B2
(45) Date of Patent: Oct. 8, 2019

(54) INTUBATION ACCESSORY

(71) Applicant: Guy Livnat, San Rafael, CA (US)

(72) Inventor: Guy Livnat, San Rafael, CA (US)

( * ) Notice: Subject to any disclaimer, the term of this patent is extended or adjusted under 35 U.S.C. 154(b) by 0 days.

(21) Appl. No.: 14/149,300

(22) Filed: Jan. 7, 2014

(65) Prior Publication Data

US 2015/0190044 A1    Jul. 9, 2015

(51) Int. Cl.
*A61B 1/267* (2006.01)
*A61B 1/05* (2006.01)
*A61B 1/06* (2006.01)
*A61B 1/00* (2006.01)
*A61M 16/04* (2006.01)
*A61B 5/08* (2006.01)

(52) U.S. Cl.
CPC .......... *A61B 1/267* (2013.01); *A61B 1/0014* (2013.01); *A61B 1/00052* (2013.01); *A61B 1/05* (2013.01); *A61B 1/0676* (2013.01); *A61M 16/0488* (2013.01); *A61B 1/00101* (2013.01); *A61B 1/00135* (2013.01); *A61B 5/082* (2013.01); *A61B 2503/20* (2013.01); *A61M 2230/432* (2013.01)

(58) Field of Classification Search
CPC .. A61B 1/267; A61B 1/07; A61B 1/05; A61B 1/00016; A61B 1/06; A61B 1/0661; A61B 1/0669; A61B 1/0676; A61B 1/0692; A61B 1/04; A61B 1/042; A61B 1/0684; A61B 1/00052; A61B 1/00002; A61B 1/00165; A61B 1/00101; A61B 1/00135; A61B 1/0014

USPC ....... 600/188, 199, 197, 179, 194, 120, 160, 600/249, 109, 175, 173; 128/200.26
See application file for complete search history.

(56) References Cited

U.S. PATENT DOCUMENTS

| | | | | |
|---|---|---|---|---|
| 4,565,187 | A * | 1/1986 | Soloway | 600/193 |
| 5,251,613 | A * | 10/1993 | Adair | 600/109 |
| 6,184,923 | B1 * | 2/2001 | Miyazaki | A61B 1/00096 348/75 |
| 6,666,819 | B2 * | 12/2003 | Heine et al. | 600/199 |
| 6,929,600 | B2 | 8/2005 | Hill | |
| 7,435,218 | B2 * | 10/2008 | Krattiger | A61B 1/00096 600/129 |
| 8,166,967 | B2 | 5/2012 | Qui | |
| 8,182,422 | B2 * | 5/2012 | Bayer | A61B 1/00016 600/109 |
| 8,416,291 | B2 | 4/2013 | Carrey et al. | |
| 8,479,739 | B2 | 7/2013 | Hirsh | |
| 2003/0078476 | A1 * | 4/2003 | Hill | A61B 1/00052 600/160 |
| 2003/0088156 | A1 * | 5/2003 | Berci et al. | 600/188 |
| 2006/0004260 | A1 * | 1/2006 | Boedeker | A61B 1/00165 600/188 |
| 2007/0049794 | A1 | 3/2007 | Glassenberg et al. | |
| 2008/0108981 | A1 * | 5/2008 | Telfair et al. | 606/4 |

(Continued)

*Primary Examiner* — Eric S Gibson
*Assistant Examiner* — Marcela I Shirsat
(74) *Attorney, Agent, or Firm* — Mark David Torche; Patwrite Law

(57) ABSTRACT

An intubation tube accessory for use in combination with an intubation tool. The accessory includes an illumination member; an imaging device; a communication mechanism configured to convey images from the imaging device to a display screen; and an intubation fixing mechanism configured for removable fixing of the intubation accessory to the intubation tool.

12 Claims, 5 Drawing Sheets

(56) References Cited

U.S. PATENT DOCUMENTS

| | | |
|---|---|---|
| 2008/0177146 A1 | 7/2008 | Chen |
| 2008/0236575 A1 | 10/2008 | Chuda |
| 2010/0249639 A1 | 9/2010 | Bhatt |
| 2010/0261967 A1 | 10/2010 | Pacey et al. |
| 2011/0028790 A1 | 2/2011 | Farr et al. |
| 2011/0245609 A1 | 10/2011 | Laser |
| 2011/0270034 A1 | 11/2011 | Mackin |
| 2012/0016197 A1 | 1/2012 | Turnbull |
| 2012/0055470 A1 | 3/2012 | Pecherer et al. |
| 2012/0078055 A1 | 3/2012 | Berci et al. |
| 2012/0116156 A1 | 5/2012 | Lederman |
| 2012/0172664 A1* | 7/2012 | Hayman ............ A61B 1/00045 600/109 |
| 2012/0296162 A1 | 11/2012 | Roze |
| 2013/0006051 A1* | 1/2013 | Stace ................ A61B 1/00071 600/109 |
| 2013/0030249 A1 | 1/2013 | Vazales et al. |
| 2014/0275778 A1* | 9/2014 | Gunday et al. ............... 600/109 |

\* cited by examiner

INTUBATION ACCESSORY

FIELD OF THE INVENTION

The present invention relates to medical devices, in particular an accessory for intubation devices to aid in the positioning and evaluation of the intubation devices.

BACKGROUND OF THE INVENTION

In cases where patients cannot breathe on their own or protect their own airway, proper placement and positioning of an artificial airway (for example an endotracheal tube) is critical in ensuring a patient receives adequate ventilation and oxygenation. This placement can be particularly difficult in irregular circumstances such as with local injury, unusual patient physicality and emergency situations in general. Being able to accurately visualize and identify the tracheal opening is a critical step in proper artificial airway placement. In many situations, if the artificial airway is not both accurately and quickly positioned, an undesirable outcome may occur.

There are several types of artificial airways that can be used to manage patients, each with its particular applications. Endotracheal tubes are introduced into the trachea in a procedure termed intubation utilizing dedicated intubation tools. Given the importance of accurate, timely and atraumatic placement, these tools include sophisticated, complex and expensive variations to assist in successful placement during difficult circumstances. However, due to their expense, such complex intubation devices are usually only available in limited quantities in any facility such as a hospital, and even less available in non-hospital settings such as EMT vehicles and medical field service facilities such as in war-zone areas. So, reliable point of care availability as well as the expense is an issue.

It is believed that the technology relevant to the present invention is disclosed in US2008/177146 (Chen); US2011/245609 (Laser); US2007/049794 (Glassenberg et al); U.S. Pat. No. 8,416,291 (Carrey et al); US2012/116156 (Lederman); US2012/296162 (Roze); US2010/261967 (Pacey et al); US2011/028790 (Farr et al); U.S. Pat. No. 8,479,739 (Hirsh); US2012/078055 (Berci et al); US2012/055470 (Pecherer et al); US2013/030249 (Vazales et al); U.S. Pat. No. 6,929,600 (Hill); US2012/016197 (Turnbull); US2008/236575 (Chuda); US2012/172664 (Hayman et al); US2011/270034 (Mackin); U.S. Pat. No. 8,166,967 (Qui); US2010/249639 (Bhatt); and WO2010/150291 (De Domenico), the contents of which are incorporated herein in their entirety.

Although intubation tools such as video laryngoscopes and video stylets are known and used, their expense limits their availability and they are not commonly a part of intubation kits. It is not uncommon, even in hospital settings that such tools are not readily available at the point of care rather such tools must be requested from another part of the hospital where stored or last in use.

Intubation tools commonly found in an intubation kit include: a laryngoscope handle with sized blades; endotracheal tubes (ETT); supra-glottal artificial breathing devices such as a laryngeal mask, laryngeal tube (e.g. King LT as it is known in the U.S.); stylets; tracheal introducers; an inflation syringe; and other common items such as face masks, catheters, etc.

SUMMARY OF THE INVENTION

The present invention relates to an accessory for intubation devices to aid in the positioning and continued evaluation thereof. The continued evaluation can refer to cases where patients have long-term artificial breathing care and it is thus important to determine that the intubation tube remains in its proper location and in proper condition.

It is an object of the present invention to provide an intubation accessory that helps with the proper introduction and placement of intubation tools.

It is another object of the present invention to provide an intubation accessory that is consistent with the recognized need in medicine today to move towards point of care (POC) solutions. It is clear that the efficacy of any intervention or tool is dependent on its availability at the needed points of care. When successful interventions are present at the points of care and shown to be cost effective, the interventions commonly become standards of care that then require consideration and adherence.

It is a further object of the present invention to provide an intubation accessory that is inexpensive and can be used in conjunction with a variety of existing intubation tools, and that is easy and convenient to use therewith. It is such features that contribute to the expected increased POC use of the present intubation accessory.

In accordance with embodiments of the present invention there is provided an intubation tube accessory for use in combination with an intubation tool. The intubation accessory includes: an illumination member; an imaging device with which the illumination member is associated; a communication mechanism operably connected to the imaging device and configured to convey images from the imaging device to a display screen; and an intubation tool fixing mechanism configured for removable fixing of the intubation accessory to the tool.

In some embodiments, the intubation tool fixing mechanism includes a generally cylindrical shape. In some embodiments, the intubation tool fixing mechanism includes at least one outwardly extending projection. In some embodiments, the intubation tool fixing mechanism includes a threaded portion. In some embodiments, the intubation tool fixing mechanism includes at least one spring. In some embodiments, the intubation tool fixing mechanism includes a foam sleeve. In some embodiments, the intubation tool fixing mechanism includes a set (kit) of tool fixing members.

In some embodiments, the accessory further includes a carbon dioxide sensor to assist intubation.

In some embodiments, the imaging device includes a video camera. In some embodiments, the image is communicated via a fiber optic tube or the like to the imaging device, which can thereby be positioned outside the patient's body.

In some embodiments, the communication mechanism includes a cable. In some embodiments, the communication mechanism includes a wireless communication system.

Herein the specification and claims the terms "tool" and "intubation tool" and their derivatives will be used to include all appropriate intubation related medical devices, including for example various artificial airways (e.g. ETTs (endotracheal tubes) and super-glottic airways as well as positioning devices therefor such as standard laryngoscopes, video and optical laryngoscopes, stylets, optical and video stylets and introducers.

Advantages of the present intubation accessory include:

Low cost whereby it can be easily added to existing intubation trays and thus made conveniently and reliably available at points of care.

Components are small and easily portable for use in different point of care scenarios.

Complements and integrates seamlessly with other standard devices and instruments utilized in airway management and tracheal intubation via standard techniques.

Does not require extensive training to use.

Components can complement and integrate with commonly available display screens including personal electronic devices (smart phones, tablets, laptops, etc.).

Can include a carbon dioxide sensing option to assist intubating with visually altered airways, which may occur due to trauma, medical illness or anatomic anomaly.

BRIEF DESCRIPTION OF THE DRAWINGS

The present invention will be understood and appreciated more fully from the following detailed description taken in conjunction with the appended drawings in which.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DETAILED DESCRIPTION OF THE INVENTION

Illustrative embodiments of the invention are described below. In the interest of clarity, not all features/components of an actual implementation are necessarily described.

The intubation accessory of the present invention will be mainly described in conjunction with an ETT, it should be understood that the present intubation accessory can also be used in conjunction with other artificial airways, for example supra-glottic airway devices that facilitate ventilation without entering the trachea, such as laryngeal masks, laryngeal tubes (known as a King LT in the U.S.) and the like. As such, for simplicity, the terms "endotracheal tube", "ETT" and their derivatives will be used herein the description and claims to include other such intubation tubes, including those listed above.

Figure 1:
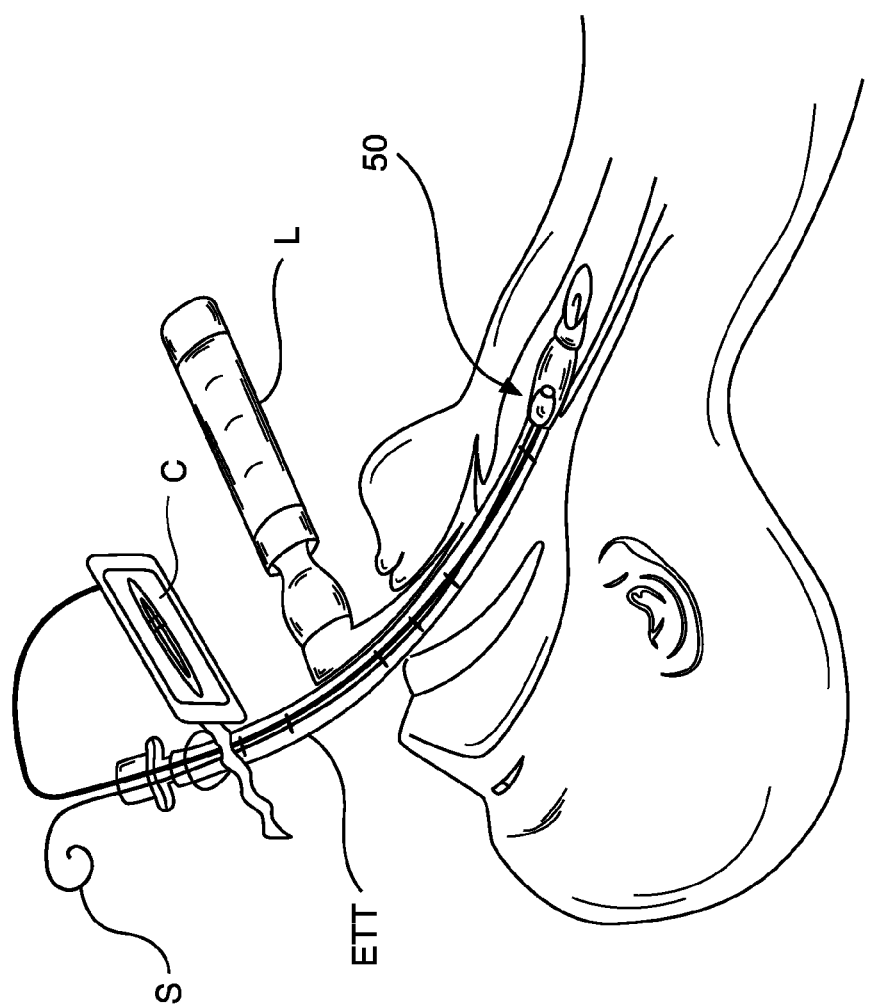
FIG. 1 shows an embodiment of an intubation accessory in accordance with the present invention, illustrated in use in conjunction with an intubation tube orally introduced into a patient, and aided by an intubation stylet and a display screen.

FIG. 1 shows an embodiment of an intubation accessory 50 in accordance with the present invention in use during oro-tracheal intubation in conjunction with an intubation tube, specifically an endotracheal tube ETT. For such intubation procedures, laryngoscopy is commonly performed with a laryngoscope L first placed in a patient's upper airway to mobilize the tongue to assist in exposing the tracheal opening. Endotracheal tube ETT is then inserted into the patient's airway and placed so as to provide air/oxygen to the patient, with the aid of a display screen C that is operably attached to intubation accessory.

Entry to the patient's airway and proper placement is often facilitated by a malleable stylet S, to pre-form the inherently flexible endotracheal tube ETT to a desired shape for the procedure, as illustrated, or a tracheal introducer N, which is a flexible rod, typically made of plastic having a profile or cross-section similar to a stylet with an optional coude tip that is used to intubate the trachea and serve as a guide over which the ETT is then introduced into position. Stylet S can be additionally utilized either as a mount for intubation accessory 50 within the endotracheal tube or to position the intubation accessory at the distal end of the ETT itself for optimal visualization. Following successful intubation, stylet S (or introducer N) is then removed, along with intubation accessory 50, or, the intubation accessory is removed shortly thereafter.

Figure 2:
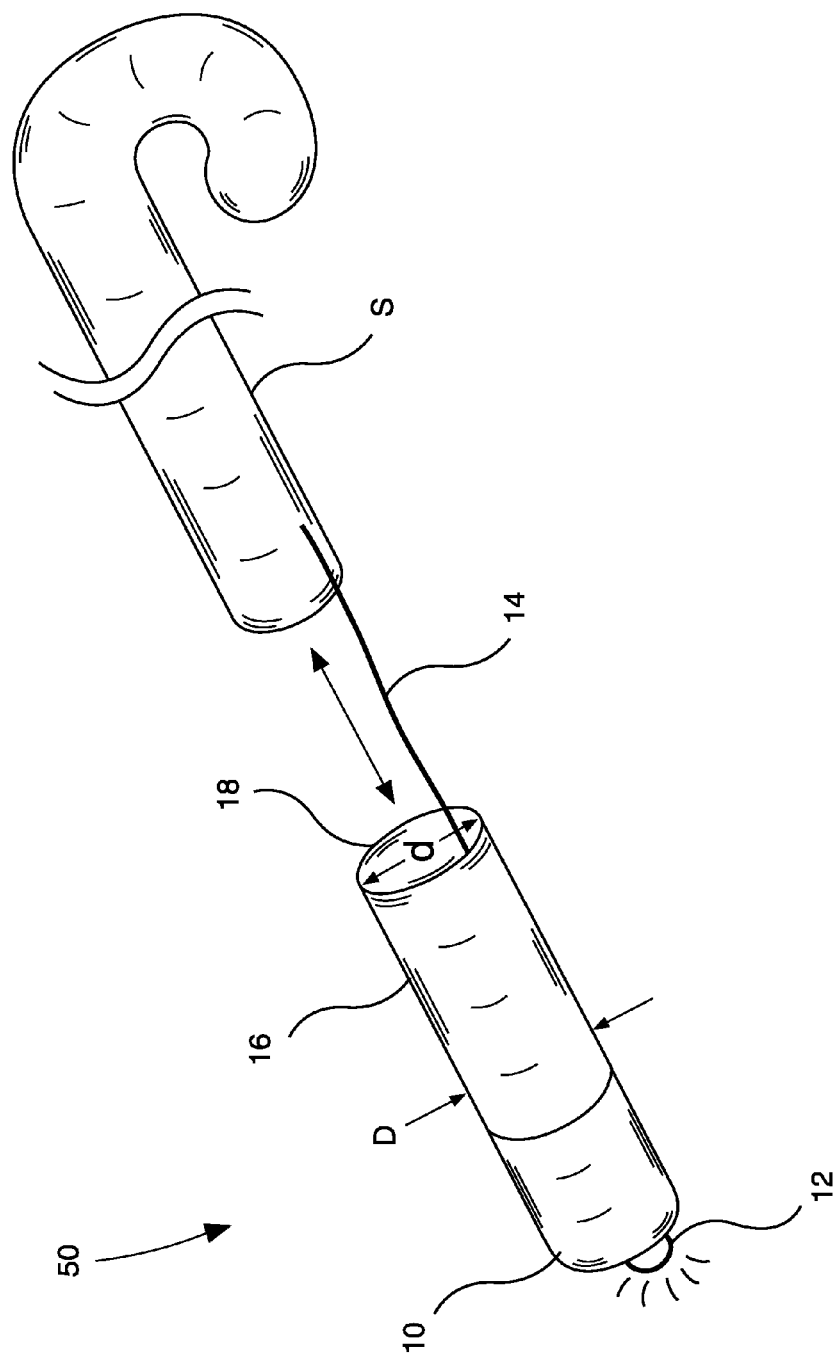
FIG. 2 shows a detailed view of the present intubation accessory including an image capturing device having an illumination member associated therewith or integral thereto, a communication mechanism operably connected to the image capturing device, and a fixing mechanism configured for interfacing the intubation accessory with the intubation tool or to appropriate positioning devices.

FIG. 2 shows a detailed view of the present intubation accessory 50 including an image capturing device 10 (e.g. video camera), typically having an illumination member 12 associated therewith or integral thereto; a communication mechanism 14, such as a cable, as illustrated, or a wireless system, operably connected to the image capturing device for communicating images from the image capturing device to a display screen, such as display screen C, to facilitate visualizing the patient's airway; and a fixing mechanism 16 configured for interfacing (i.e. removably fixing) intubation accessory 50 with the intubation tool (e.g. endotracheal tube ETT) or to appropriate positioning devices such as stylet S, introducer N, or the like. Illumination member 12 can be configured as a combination of an illumination source and image capturing/camera lens.

Image capturing device 10 (including illumination member 12 where applicable) and communication mechanism 14 can be collectively considered as components of a data acquisition unit of intubation accessory 50. In some embodiments, a fiber optic tube, or the like, is configured to be attachable to an intubation tool and communicates with imaging capture device 10, which can thereby be positioned external of the patient.

In this embodiment, fixing mechanism 16 has a generally cylindrical shape defining a tubular cavity 18 configured to receive the distal end of stylet S in order to place intubation accessory 50 onto the end of the stylet (or introducer N), for example. In some embodiments, fixing mechanism 16 is made of a relatively soft or flexible plastic, or the like, thereby providing some flexible quality to help provide ease and range of fit.

It should be understood that fixing mechanism 16 of intubation accessory 50 may have a range of sizes to thereby suit ETT's and other artificial airways such as super-glottic airways as well as intubation tools/positioning devices such as stylet S and introducer N of different sizes. In this regard, it should be understood that (a) the outer diameter "D" of fixing mechanism 16 may be dimensioned to facilitate a somewhat snug fit within the ETT, while being reasonably easily removable therefrom; and/or (b) the inner diameter "d" of cavity 18 may be dimensioned to facilitate a similar fit over stylet S or introducer N. After placement of the ETT, intubation accessory 50 is removed, just as a video stylet or video introducer would be removed.

In some embodiments, intubation accessory 50 comes with a kit or set of variously sized and/or type fixing mechanisms 16 to facilitate the above-mentioned fit, as will be understood with respect to embodiments described below.

Figure 3:
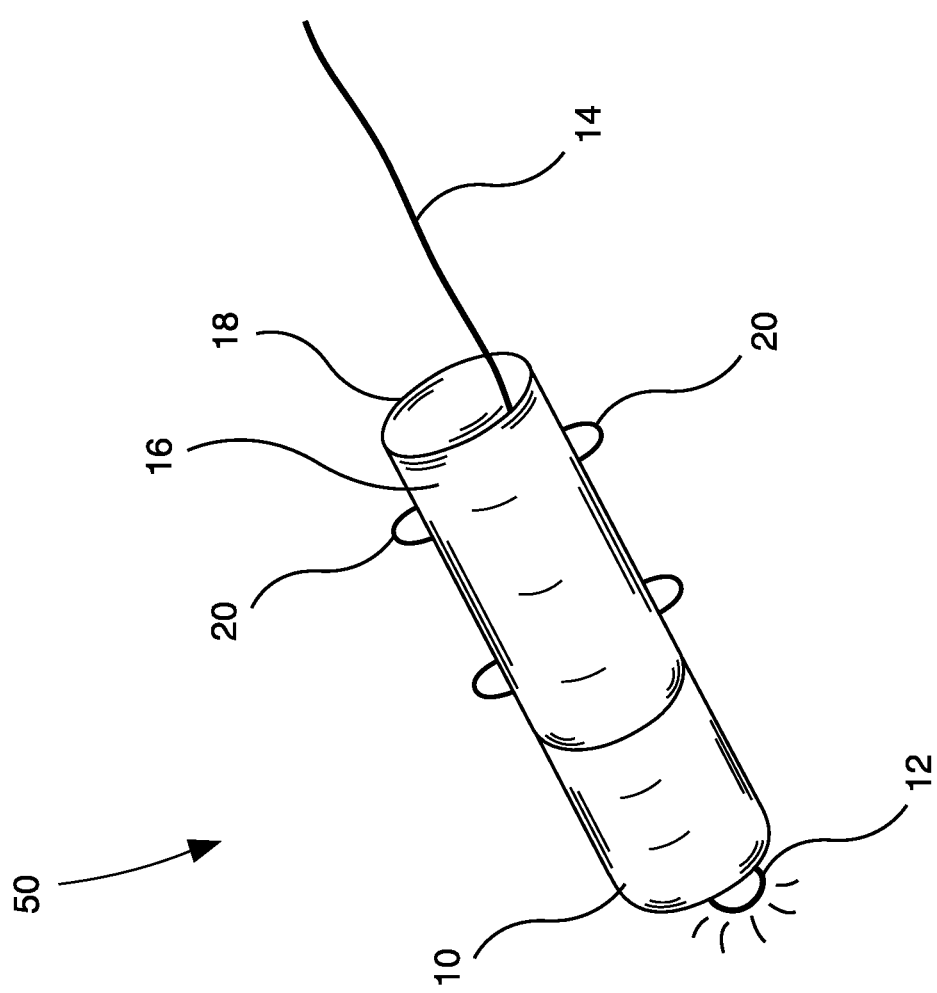
FIG. 3 is a perspective view of the present intubation accessory of FIG. 2.

FIG. 3 shows another embodiment of intubation accessory 50 in accordance with the present invention, particularly useful for nasal introduction intubation procedures. Stylets, such as stylet S, and introducers, such as introducer N, are not typically used in nasal entries due to the geometry of the nasal passageway. Thus, intubation accessory 50 must be fixed to the inner wall of the ETT. To improve the quality of the fit (snugness yet removability), in this embodiment, fixing mechanism 16 includes an externally facing ETT interface mechanism, in the present embodiment including at least one and typically a plurality of bendable wings or protrusions 20 protruding from the outside of the fixing mechanism. Protrusions 20 are configured to interface with the inner wall of the ETT to thereby help removably fix intubation accessory 50 to thereto. Protrusions 20 are illustrated as protruding generally radially outward from fixing mechanism 16, which is a typical embodiment, and as having a nub-like shape, which is a typical configuration; however, should not be considered as limiting as various shapes and angles of protrusion can be used.

Figure 4:
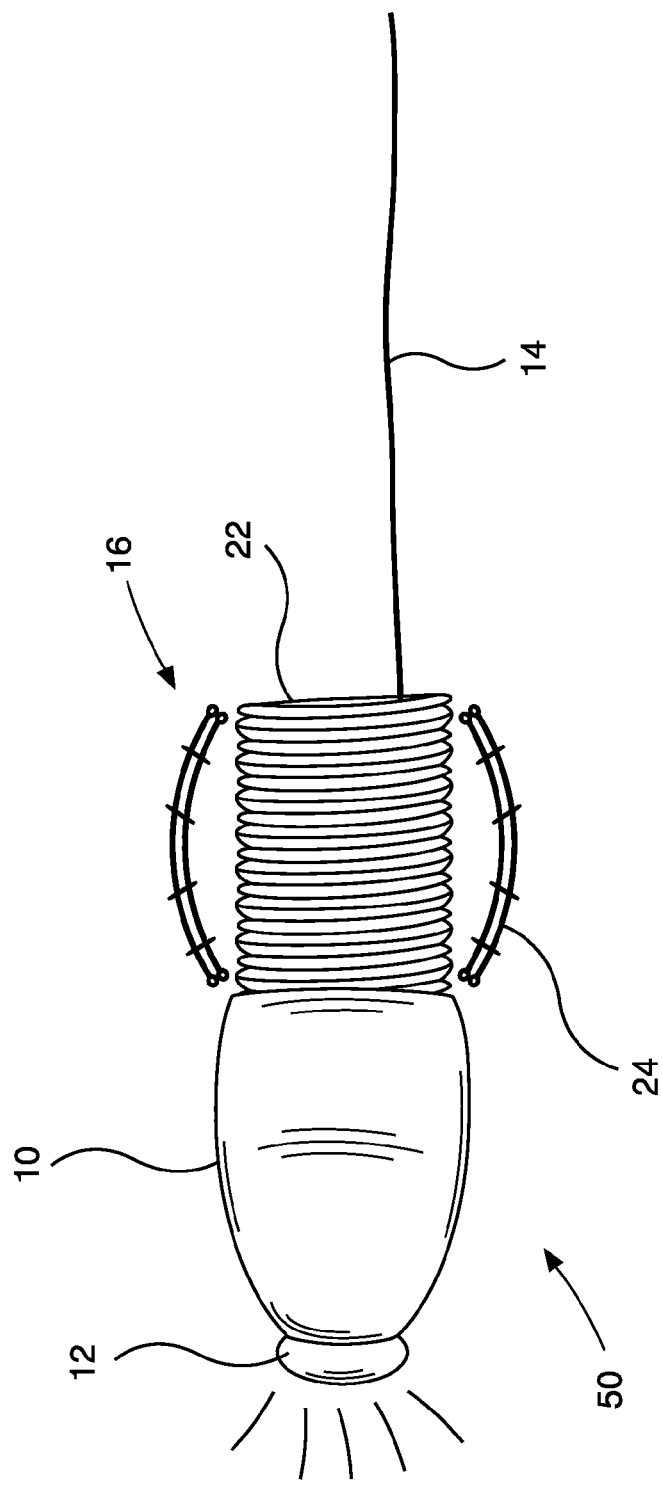
FIG. 4 is a side view of another embodiment of the intubation accessory in accordance with the present invention, particularly useful for nasal introduction intubation procedures.

FIG. 4 shows another embodiment of intubation accessory 50 wherein fixing mechanism 16 includes a threaded portion 22 to which an ETT interface component can be attached, such as one or more adjustable leaf-like springs 24. Spring 24 can be generally cylindrically shaped and screwed onto threaded portion 22, either already assembled or threaded shortly prior to intubation. Again, such a design is particularly useful for nasal introduction intubation procedures, although threaded portion 22 can also be formed in a cylindrical shape with a cavity, such as cavity 18 so that stylet S or introducer N can be inserted therein. It should be understood that other components having similar function to spring(s) 24 can be used. One example of another such component is a foam sleeve 26 (FIG. 5) that can be attached to the outside of fixing mechanism 16 or slipped over the fixing mechanism.

Figure 5:
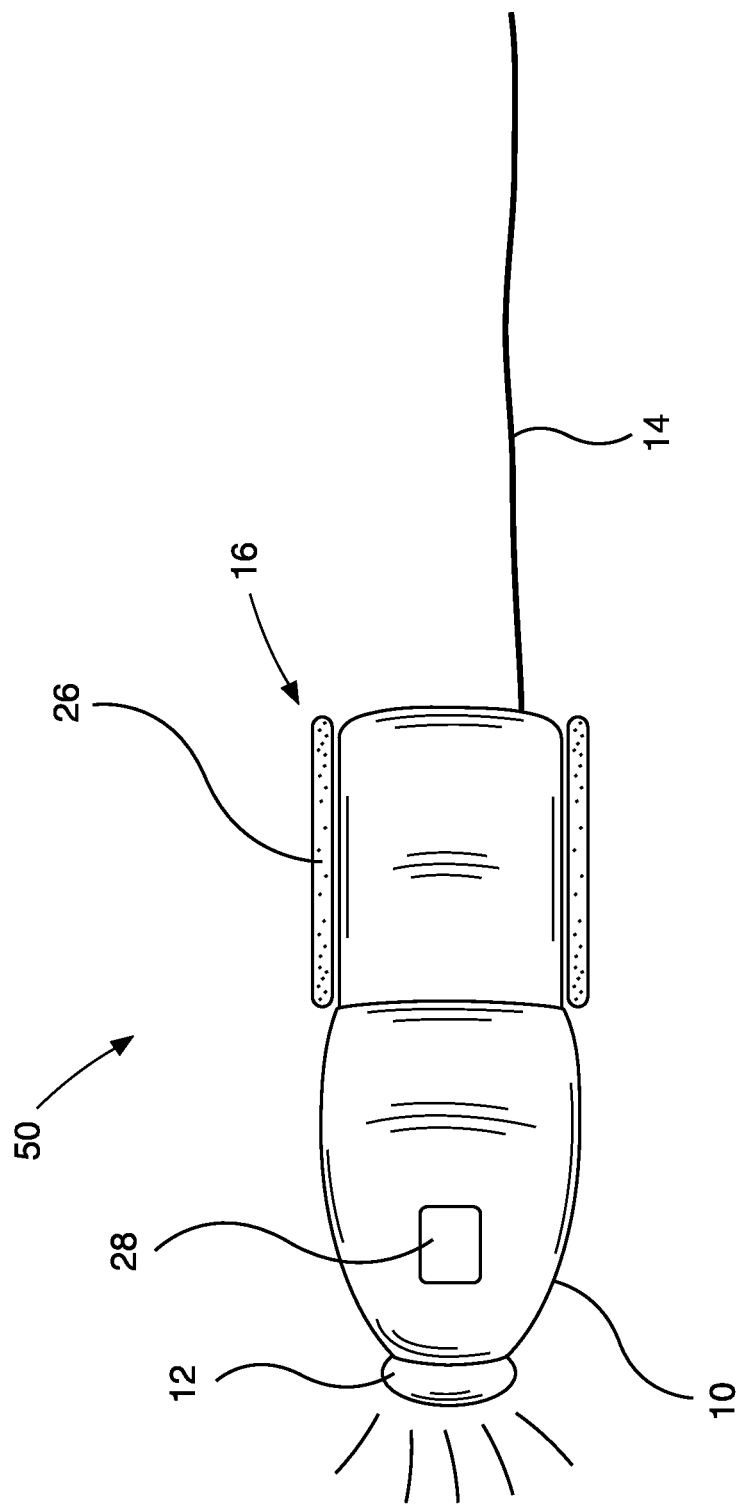
FIG. 5 is a side view of another embodiment of the intubation accessory in accordance with the present invention, also particularly useful for nasal introduction intubation procedures.

As schematically illustrated in FIG. 5, in some embodiments, intubation accessory further includes a carbon dioxide sensor 28, which can be useful for helping detect carbon dioxide exiting the trachea and thereby helping identify an altered tracheal opening to assist in the proper placement of the ETT.

To preserve the option of intubation accessory 50 having broad implementation flexibility, fixing mechanism 16 is preferably configured to be both removably fixed to an ETT as well as mountable on the distal end of a stylet or introducer, and for such purpose the fixing member may have both a cavity as well as protrusions 20 (or threaded portion 22 and/or spring 24 or foam sleeve 26, or the like).

Due to its relatively low cost, in some embodiments, it is envisioned that the intubation accessory 50 will be implemented as a disposable one-time use device. On the other hand, in some embodiments, the intubation accessory 50 is configured and designed to be sterilized after use so that the accessory is a multi-use device.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. A medical apparatus for assisting in the insertion of a respiratory tube in a subject comprising:
  a substantially cylindrical sleeve with a distal end affixed to an outward-facing illumination device and a corresponding forward-facing imaging device, said sleeve comprising an open proximal end connecting a tubular cavity to an outer space, said open proximal end to slidingly receive therethrough a distal end of a respiratory tube insertion tool; and
    said sleeve including an inner surface around said tubular cavity configured to wholly slide over and removably affix itself to said distal portion of said respiratory tube insertion tool; and
  a communication mechanism operably connected to said imaging device and configured to convey images from said imaging device to a display device.

2. The apparatus of claim 1, wherein said sleeve comprises at least one outwardly extending projection configured to abut an inner wall surrounding a lumen in the respiratory tube.

3. The apparatus of claim 1, wherein said sleeve comprises a threaded portion for mating with a component configured to abut an inner wall surrounding a lumen in the respiratory tube.

4. The apparatus of claim 1, wherein said sleeve comprises at least one spring configured to abut an inner wall surrounding a lumen in the respiratory tube.

5. The apparatus of claim 1, wherein said sleeve comprises a foam sleeve configured to abut an inner wall surrounding a lumen in the respiratory tube.

6. The apparatus of claim 1, further comprising a carbon dioxide sensor to assist in the insertion.

7. The apparatus of claim 1, wherein the imaging device includes a video camera.

8. The apparatus of claim 1, wherein the communication mechanism includes a cable.

9. The apparatus of claim 1, wherein the communication mechanism includes a wireless communication system.

10. The apparatus of claim 1 wherein said sleeve is configured to affix the apparatus inside a lumen of an airway tube of a supra-glottic airway device.

11. The apparatus of claim 10 wherein said supra-glottic device comprises a laryngeal mask.

12. The apparatus of claim 1 wherein the apparatus is disposable.

* * * * *